United States Patent
Lin et al.

(10) Patent No.: US 6,627,775 B2
(45) Date of Patent: Sep. 30, 2003

(54) PROCESS FOR MANUFACTURING GASOLINE ADDITIVES OF ESTER-FREE POLYOXYALKYLENE AMIDE

(75) Inventors: Jiang-Jen Lin, Taichung (TW); Yung-Sheng Ho, Chiai (TW); Wei-Shiun Ku, Chiai (TW); Wen-Jei Shiu, Chiai (TW); Che-Nan Lee, Chiai (TW)

(73) Assignee: Chinese Petroleum Corporation, Taipei (TW)

( * ) Notice: Subject to any disclaimer, the term of this patent is extended or adjusted under 35 U.S.C. 154(b) by 0 days.

(21) Appl. No.: 10/056,014

(22) Filed: Jan. 28, 2002

(65) Prior Publication Data

US 2003/0163954 A1 Sep. 4, 2003

(51) Int. Cl.$^7$ ............................................. C07C 233/05
(52) U.S. Cl. ..................... 564/224; 564/136; 564/159; 564/215; 44/418; 44/419
(58) Field of Search ................................ 564/159, 215, 564/224, 136; 44/418, 419

(56) References Cited

U.S. PATENT DOCUMENTS 6,312,481 B1 * 11/2001 Lin et al. ..................... 44/418
6,454,818 B1 * 9/2002 Lin et al. ..................... 44/418

* cited by examiner

Primary Examiner—Shailendra Kumar
(74) Attorney, Agent, or Firm—Rosenberg, Klein & Lee

(57) ABSTRACT

An improved process to prepare poly(oxyalkylene)amide for gasoline additives involves three consecutive reactions. The reactions are (1) amidation of water-soluble low molecular weight of polyalkylene polyamine with alkyl acetate at an elevated temperature under $N_2$ pressure to convert amines to amides, (2) Butoxylation of the amides with 1,2-epoxybutane to prepare the poly(oxyalkylene) amides, and (3) selective hydrolysis of in situ poly(oxyalkylene)-amine-ester-amides into poly(oxyalkylene)-amine-alcohol-amides and removal of acetic acid byproducts, via acid/base hydrolysis and water extraction procedures. The process step of selective hydrolysis is essential for removal the harmful composition of poly(oxyalkylene)-amine-ester-amides in resulting the better performance of the additive, particularly the positive engine's octane requirement or reducing the combustion chamber deposits. More specifically the butoxylation process generally produces poly(oxyalkylene)amides and poly(oxyalkylene)esters via an exchange reaction (trans-amidation/trans-esterification) and the poly(oxyalkylene)esters in the product mixtures is removed to obtain better performance products.

6 Claims, 1 Drawing Sheet

PROCESS FOR MANUFACTURING GASOLINE ADDITIVES OF ESTER-FREE POLYOXYALKYLENE AMIDE

FIELD OF INVENTION

This invention relates to a method of a gasoline additive producing and more particularly a process for manufacturing gasoline additives of ester-free polyoxyalkylene-amide which is advantageous for decreasing intake valve deposits, decreasing octane requirements, controlling internal combustion chamber deposits and improving fuel efficiency.

BACKGROUND OF THE INVENTION

Many additives are known to be added in gasoline in order to prevent or reduce deposit formation. Recent related prior art is cited below:

Polyoxyalkylene amide:
  U.S. Pat. No. 5,352,251 (Oct. 4, 1994) to Shell Oil Company, "Ring polyoxyalkylene amide as gasoline additives".
  U.S. Pat. No. 5,693,107 (Dec. 2, 1997) to Shell Oil Company, "Hydantoin polyoxyalkylene amide as gasoline additives".
  U.S. Pat. No. 5,492,546 (Feb. 20, 1996) to Shell Oil Company, "Fuel composition".
  U.S. Pat. No. 5,507,843 (1996) to Shell Oil Company, "Fuel composition".
  U.S. Pat. No. 5,489,315 (1996) to of Shell Oil Company, "Hydantoin polyether polyol as gasoline additives".
  U.S. Pat. No. 5,458,661 (1995) to Shell Oil Company, "Fuel composition".
  U.S. Pat. No. 5,458,660 (1995) to Shell Oil Company, "Fuel composition".

Polyoxyalkylene amines:
  U.S. Pat. No. 5,057,122 (Oct. 15, 1991) to Mobil Oil Company, "A dilsocyanate derivatives composition as fuel additives and lubricants".
  Other documents include U.S. Pat. No. 4,604,103 (1986) to Chevron, U.S. Pat. No. 5,112,364 (1992) to BASF, U.S. Pat. Nos. 5,286,266 & 5,286,267 (1994) to Texaco, U.S. Pat. Nos. 5,286,478 (1993) & 5,203,879 (1993) & 4,810,261 (1989) & 4,747,851 (1988) to Texaco.

Polyoxyalkylene amine carbamates:
  U.S. Pat. No. 5,321,460 (1994) to Chevron, "Linear propylene oxide of polyoxyalkylene amine carbamates as a fuel composition".
  And also U.S. Pat. No. 5,322,539 (1994), 5,321,460 (1994), 5,192,335 (1993) to Chevron, U.S. Pat. No. 423,321 (1980) to Chevron, U.S. Pat. No. 5,103,041 (1992) to British Petroleum U.S. Pat. No. 4,568,358 (1986) to Chevron.

Others
  U.S. Pat. No. 5,296,003 (Mar. 22, 1994) to Chevron, U.S. Pat. No. 5,298.039 (Mar. 29, 1994) to BASF, disclosing a gasoline fuel composition comprised a nitro-detergent and polyester as a carried oil compound, wherein polyester compound starter is dialkyl phenol.
  U.S. Pat. No. 5,246,006 (1993) to Exxon and 5,089,029 (1992) to Kao Corporation, regarding acrylonitrile reaction to form a Guerbet alkyletheramino-alchohol by addition process and reducing process.

However, the above prior arts never mention the formation of a byproduct, polyoxyalkylene amide-ester as follows:

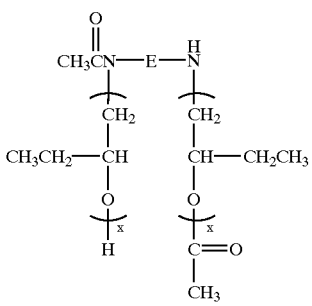

Which may reduce the performance of the other gasoline additives in lessening intake valve deposits or increasing the octane requirement.

SUMMARY OF THE INVENTION

The object of the present invention is to provide a process for manufacturing gasoline additives of ester-free polyoxyalkylene amides which are advantageous for decreasing intake valve deposits, octane requirements, controlling combustion chamber deposits and improving fuel efficiency.

The present invention is directed to manufacturing gasoline additives of ester-free polyoxyalkylene amide from a three-step process, as in FIG. 1:

A. Amidation of low-molecular-weight polyoxyalkylene amine with ethyl acetate to form the corresponding amides.

B. Alkoxylation of the amide with 1,2-epoxybutane to form polyoxyalkylene amide and unavoidable byproducts as below:

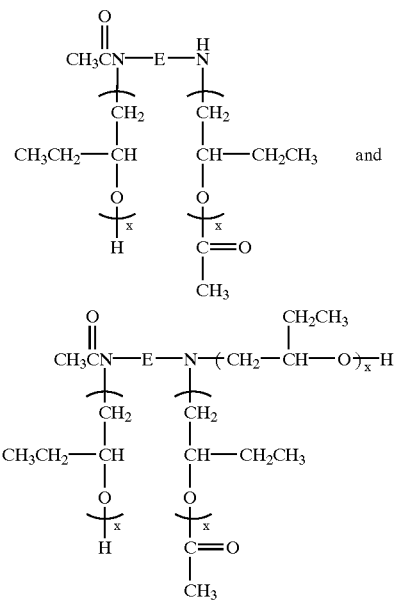

C. Selective hydrolysis of the above mixtures to remove the amide-ester byproducts and recover the desired amide alkoxylates.

The essential analytical method is to use FT-infrared to identify the presence of the byproducts, hence the ester-free amides should be free of the following indicative 1735 cm$^{-1}$ absorption:

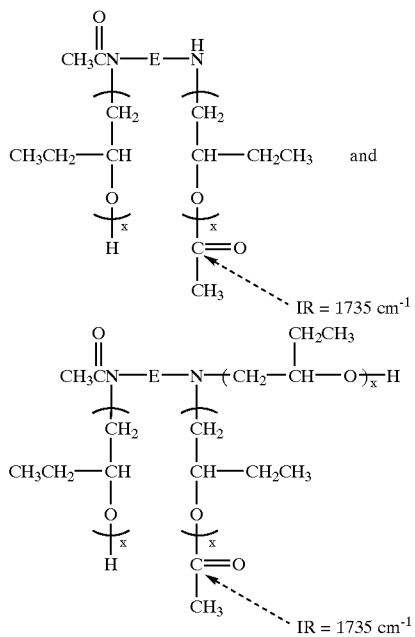

Those ester-amide byproducts are proven to be harmful to the engine. Therefore, in step(c), the removal of the esters is important to manufacture the effective gasoline additives. The hydrolysis must be selective to remove only the ester byproducts but remaining the following desired amide alkoxylate with the indicative infra-red absorption at 1650 cm$^{-1}$.

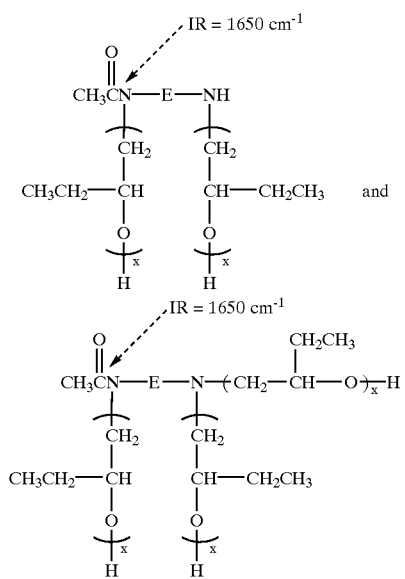

The selective hydrolysis process is one of essential part of this invention. For example, the amidation and alkoxylation to made diethylenetriamine-triamide-butoxylate (DETA triamide-BO) and its contaminated esters should be subjected to the selective hydrolysis step to remove the ester functional group. The process required the treatment of the product mixtures with 8 to 12 wt % HCl, preferably 10% at 90 to 100° C. under the refluxing condition. The process is carefully monitored by analyzing the disappearance of ester C=O Absorption peak (1735 cm$^{-1}$) by IR. The ester functionalities are removed and a polyalkylene amide or amine-amide is generated. The desired composition is further analyzed by a gel permeation chromatography showing a narrow molecular weight distribution.

The tests of intake valve coking simulator (IVCS), and thermal decomposition test and octane requirement reduction (ORR) showed excellent results for the ester-free products.

BRIEF DESCRIPTION OF THE DRAWINGS

The three-step process is further described by using chemical structures and equations in FIG. 1, which is a scheme describing the embodiment of the invention.

DETAILED DESCRIPTION OF THE PREFERRED EMBODIMENTS

EXAMPLES

Figure 1:
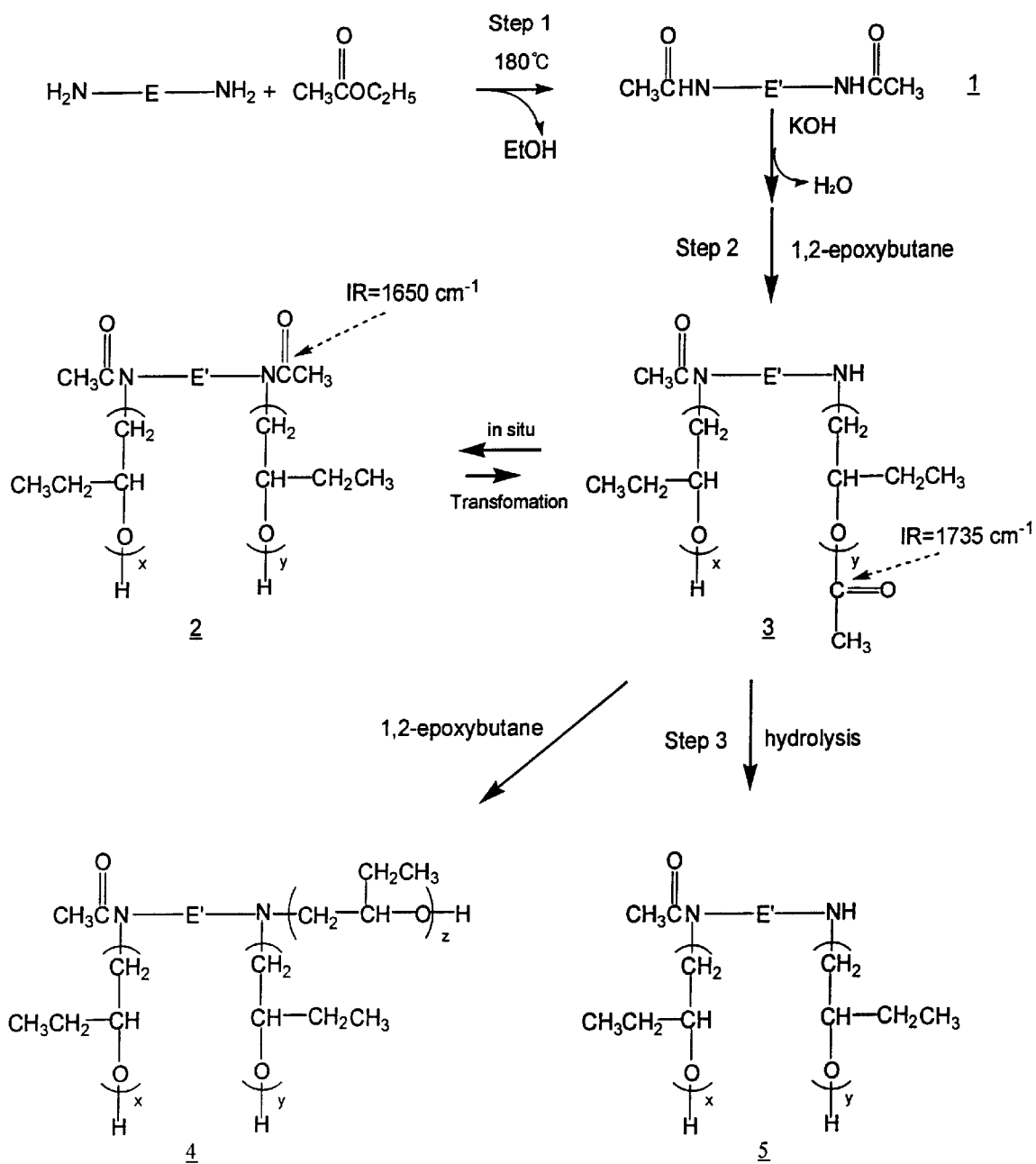

Experimental Procedures for the Synthesis of Ester-free Poly(oxyalkylene)-amide Gasoline Additives Example 1

(Step 1) The Preparation of Triamide From Diethylenetriamine (DETA) and Ethyl Acetate 1. A mixture of DETA (35.20 g, 0.34 moles) and ethyl acetate (176 g) were charged into a one-liter autoclave.
2. The autoclave was sealed and was purged off air by pressuring and depressurizing with nitrogen at 500 psi to 50 psi several times, while stirring.
3. Under an initial nitrogen pressure of 500 psi, the mixture was heated slowly to 180° C. and kept at this temperature for over 14 hours. During the process, a maximum pressure of 740 psi at 180° C. was observed. Then, the pressure lowered with time due to the condensation of ethyl acetate from vapor phase into liquid phase. The lowering of pressure stopped after about 8 hours. The mixture was then cooled to ambient temperature, excessive gas was vented and the product was recovered as a light brown liquid. The crude product was rotovapped at 70° C. to remove ethyl acetate. The weight of the crude product was 207 g. As referred to FIG. 1, the crude product is compound 1.

Example 2

(Step 2) Butoxylation of DETA-Triamide

1. A mixture of DETA-triamide (13.74 g, 0.06 moles), potassium hydroxide (0.27 g) and 1,2-epoxybutane (82.22 g, 1.11 moles) were charged into a one-liter autoclave.
2. The autoclave was sealed and was purged off air by pressuring and depressurizing with nitrogen at 500 psi to 50 psi several times, while stirring.
3. Under an initial nitrogen pressure of 500 psi, the mixture was heated slowly to 120° C. and kept at this temperature for over 17 hours. During the process, a maximum pressure of 639 psi at 120° C. was observed. Then, the pressure lowered with time due to the condensation of 1,2-epoxybutane from vapor phase into liquid phase.
4. The lowering of pressure stopped after about 9 hours. The mixture was then cooled to ambient temperature, excessive gas was vented and the product was recovered as a light brown liquid. The crude product was rotovapped at 70° C. to remove 1,2-epoxybutane. The weight of the crude product was 91.87.
5. The product was subjected to GPC, NMR and IR analyses after washing out K⁺ with distilled water. GPC analysis indicated an average molecular weight of Mw=1435. As referred to FIG. 1, the crude products are a mixture of compounds 2, 3, and 4.

Example 3

(Step 3) Selective Hydrolysis of the Butoxylation Product of Triamide with 10% HCl Solution 1. A mixture of the butoxylation product of triamide (20 g) and 10% HCl solution (80 g) were charged into a beaker and mixed with a magnetic stirrer while refluxing at 90–100° C.
2. During the reaction, small amount of samples was taken from the beaker and was subjected to IR analysis in order to monitor the reaction. After about 8 hours, disappearance of IR absorption peak characteristic of C=O (1735 $cm^{-1}$) indicates the completion of the reaction.
3. Turn off the heater and stop the reaction. The mixture was then cooled to ambient temperature. A mixture of 40 ml pure water and 40 ml toluene was used to extract and dilute the acidity of the solution.
4. Using 40 ml of 1 N NaOH to neutralize the toluene layer and discarded the water layer.
5. Using 40 ml of water to extract NaOH in the upper layer twice.
6. The crude product was rotavapped at 70° C. to remove 1,2-epoxybutane and recovered to be 12.5 g. The yield was 60%. After washing out K⁺ with distilled water, the product was subjected to GPC, NMR and IR analyses. GPC analysis indicated an average molecular weight of Mw=1375.

Test Results

In each of the following tests, the base fuel was an unleaded gasoline that contained no additives. The Gemini poly(oxyalkylene)diamide compounds utilized were prepared as indicated by Example number and were used at the concentration indicated in ppm by mg/ml. The test employed are described hereinafter and the results of the various tests are set forth in tables below. The following tests may also contain one or more additional detergents. When additional detergents are used, the fuel composition will comprise a mixture of a major amount of hydrocarbon in the boiling range as indicated, a minor amount of an additional detergents selected from polyalkenyl amine, poly(oxyalkylene) carbamates and mixture thereof. Since some benefits may be derived from using carrier fluid, some tests by incorporating 100 or 200 mg/l of polyether type carrier fluid were also evaluated.

Intake Valve Coking Simulator (IVCS) Test

The IVCS test is a measure of the deposit formation on the hot ramp, the results denotes the tendency of the additive package dispersing the carbonaceous deposit generated on the film. The deposit simulator results were shown to correlate with BMW intake-valve deposit test. The test fuel is pumped to an injector consisting of a water-cooled hypodermic needle. The ramp is heated at the elevated end with six electric heaters and thermally insulated to achieve a temperature difference of 400° C. at the elevated end and 120° C. at the bottom of the ramp. In the IVCS test equipment, four parallel test cells were provided, so that four different samples can be tested at the same time.

The properties of the base fuel are as follows:

| Property | Value |
|---|---|
| IBP | 40.3° C. |
| 50% BP | 108.1° C. |
| 90% BP | 163.5° C. |
| Aromatics | 41.6 vol. % |
| Olefins | 2.8 vol. % |
| Saturates | 48.1 vol. % |
| MTBE | 7.5 vol. % |
| RON | 92 |

The test conditions are as follows:

| | |
|---|---|
| Test fuel volume: | 250 ml |
| Test fuel flow: | 0.83 ml/min. |
| Ramp slop: | 5° |
| Stainless steel film | 47 mm W × 10110 mm L × 0.02 mm T |

Before test, stainless steel films were thoroughly cleaned with solvent (50% n-hexane and 50% acetone), then put the films in an oven at a temperature of 120° C. for 1 hour to remove solvent and water. New test film were weighed and installed, tests were run for a period of about 5 hours. At the end of each test, the film was removed, cleaned and re-weighed. Weight gain of the deposit on the film is the IVCS index, reported in mg/250 ml. Generally, the less the deposit formed, the better the intake valve detergency performance of the gasoline or additive tested was. Experience has shown that gasoline giving deposit less than about 3.0 g/250 ml provides good intake valve detergency performance.

TABLE 1

| Compound Example # | Concentration mg/l | Additional detergent conc. mg/l | Additional carrier fluid conc. mg/l | Deposit mg/250 ml |
|---|---|---|---|---|
| — | 0 | — | 0 | 12.0 ± 0.3[1] |
| — | 0 | — | 200 | 6.5 |
| 2 | 200 | — | 0 | 15.8 |
| 2 | 200 | — | 200 | 2.9 |
| 3 | 200 | — | 0 | 20.5 |
| 3 | 200 | — | 200 | 5.0 |
| 3 | 100 | 100(GKA67[2]) | 0 | 2.8 |
| 3 | 100 | 50(GKA67[2]) | 200 | 3.4 |

[1]0.3 denotes 95% level of confidence interval (24 data points)
[2]GKA67-polyalkenyl amine available commercially from BASF.

Thermal Decomposition Test

In order to evaluate the CCD performance of the novel gasoline additive, thermal decomposition test was conducted under following test conditions and sequences:

| | |
|---|---|
| Test sample weight: | 0.2 g |
| Container: | Ceramic crucible |
| | Size: 5 cm diameter, 0.5 cm depth |
| Oven: | Lindberg, Blue M-Model 848 |
| Test condition: | 300° C., 60 min. |

The results of the thermal decomposition tests are set forth in table 2.

TABLE 2

| Compound Example # | Concentration (wt. %) | Residue (wt. %) 300° C., 60 min. |
|---|---|---|
| 2 | 100 | 2.0 |
| 3 | 100 | 4.4 |
| OGA480[1] | 100 | 2.5 |
| PEA-Texaco[2] | 100 | 4.1 |
| OGA472[3] | 100 | 42.4 |

[1]OGA480—a poly(oxyalkylene)carbamate available commercially from Oronite.
[2]PEA—polyester amine available commercially from Texaco, for comparison use only.
[3]OGA472—polyalkyenyl amine available commercially from Oronite.

It is well known that the fewer residues formed at 300° C., the better combustion chamber deposit control and low ORI value are. OGA-480 controls engine ORI whereas OGA-472 tends to cause engine ORI. From the above thermal data, Example 2 and 3 have nearly the same performance in CCD control better than OGA 480.

Method for Octane Requirement Reduction Testing

The purpose of octane requirement reduction test is to provide a method of determining the effect of various gasoline components and additives upon the octane requirement of the engine.

The experiment rig consisted mainly of a single-cylinder Waukesha CFR (Cooperative Fuel Research) gasoline engine, a pressure transducer, a charge amplifier, and a FFT (Fast Fourier Transform) signal analyzer. The critical CFR engine parameter and engine operating conditions are shown as follows.

| Engine: | Waukesha CFR engine |
|---|---|
|  | 612 cc, single cylinder, carburator |
| Test conditions: | Air inlet temperature: 38° C. |
|  | Compression ratio: 7.0 |
|  | Air/fuel ratio: 13.5 |
|  | Spark timing: 23 BTDC |
|  | Cooling temperature: 100° C. |

Before starting of octane requirement reduction (ORR) test, the CFR engine has been dirty up after running engine test of accumulating 200 hours. Then the initial octane requirement (ONR) of fuel for the CFR engine is determined by detecting knock. The primary reference fuels (PFR) of a variety of RON blended by isooctane and normal heptane are used as ONR rating fuels. If the light engine knock occurred, the FFT signal analyzer will display a signal whose amplitude is higher than −53 dBVr in spectrum correlated by ear rating. The knock signal of the CFR engine comes out around the frequency of 5.8–6.4 kHz. The criterion of determining the ONR value for the engine was determined on the 25 percentage of light knock occurring frequency of 100 consecutive power cycles obtained using an intrapolation method.

Then the 60-hour engine ORR test starts to run using base fuel prepared by blending gasoline with 200 mg/l of Example 2 and 3 additives. Properties of the base fuel are shown as follows.

| Property | Value |
|---|---|
| IBP | 40.0° C. |
| 50% BP | 108.6° C. |
| 90% BP | 170.5° C. |
| Aromatics | 26.8 vol. % |
| Olefins | 25.1 vol. % |
| Saturates | 48.1 vol. % |
| RON | 95 |

During the test, the duration of rating interval for ONR is typically eight hours. When the engine test was completed, the final ONR was rated again. The total ORR was calculated as the difference between the ONR numbers of the engine at the beginning and the end of the engine test.

The ORR performances of two additives, Example 2 and 3, have been measured. At the beginning of ORR test, the initial ONR of the CFR engine is 90.5 RON. The test results for additives are shown in Table 3. It can be seen that example 2 shows no ORR performance. After completion of the ORR test for Example 2, the engine was dirty up using base fuel by 24 hours until the ONR condition became 90.7 RON. Then the ORR test for Example 3 was started. The ORR performance for additive Example 3 is 2.1 RON compared with Example 2 as shown in Table 3.

TABLE 3

| Test fuel | Run 1 Base fuel + Example 2 (RON) | Run 2 Base fuel + Example 3 (RON) |
|---|---|---|
| 1. ONR at 0 hours | 90.5 | 90.7 |
| 2. ONR at 30 hours | 90.1 | 89.3 |
| 3. ONR at 60 hours | 90.6 | 88.6 |
| 4. ORR = ONR @ 0 hrs − ONR @ 60 hrs | | |

While the present invention has been described in connection with what is considered the most practical and preferred embodiments, it is understood that this invention is not limited to the disclosed embodiments but is intended to cover various arrangements included within the spirit and scope of the broadest interpretations and equivalent arrangements.

What is claimed is:

1. A method for producing ester-free poly(oxyalkylene) amide comprising the steps of:
   a. amidation of water-soluble, low molecular weight polyalkylene polyamine with alkyl acetate at an elevated temperature to prepare polyalkylene polyamides;
   b. preparing a poly(oxyalkylene)amide by alkoxylation of said amides with 1,2-epoxyalkylene; and
   c. selective hydrolysis of said poly(oxyalkylene)amide to convert ester to alcohol to obtain ester-free poly (oxyalkylene)amide as gasoline additive.

2. The method as claimed in claim 1, wherein the alkyl acetate is selected from the group consisting of methyl acetate, ethyl acetate, propyl acetate, butyl acetate and C5 to C20 hydrocarbyl acetate.

3. The method as claimed in claim 1, wherein the weight average molecular weight of the polyalkylene polyamine is from about 600 to 4000.

4. The method as claimed in claim 1, wherein 1,2-epoxyalkylene is 1,2-epoxybutane.

5. The method as claimed in claim 1, wherein polyalkylene polyamine is diethylenetriamine.

6. The method as claimed in claim 1, wherein the step of selective hydrolysis uses a 5–20% HCl solution.

* * * * *